Jan. 27, 1970 G. MERRILL Plant Pat. 2,965
PEACH TREE
Filed May 20, 1968
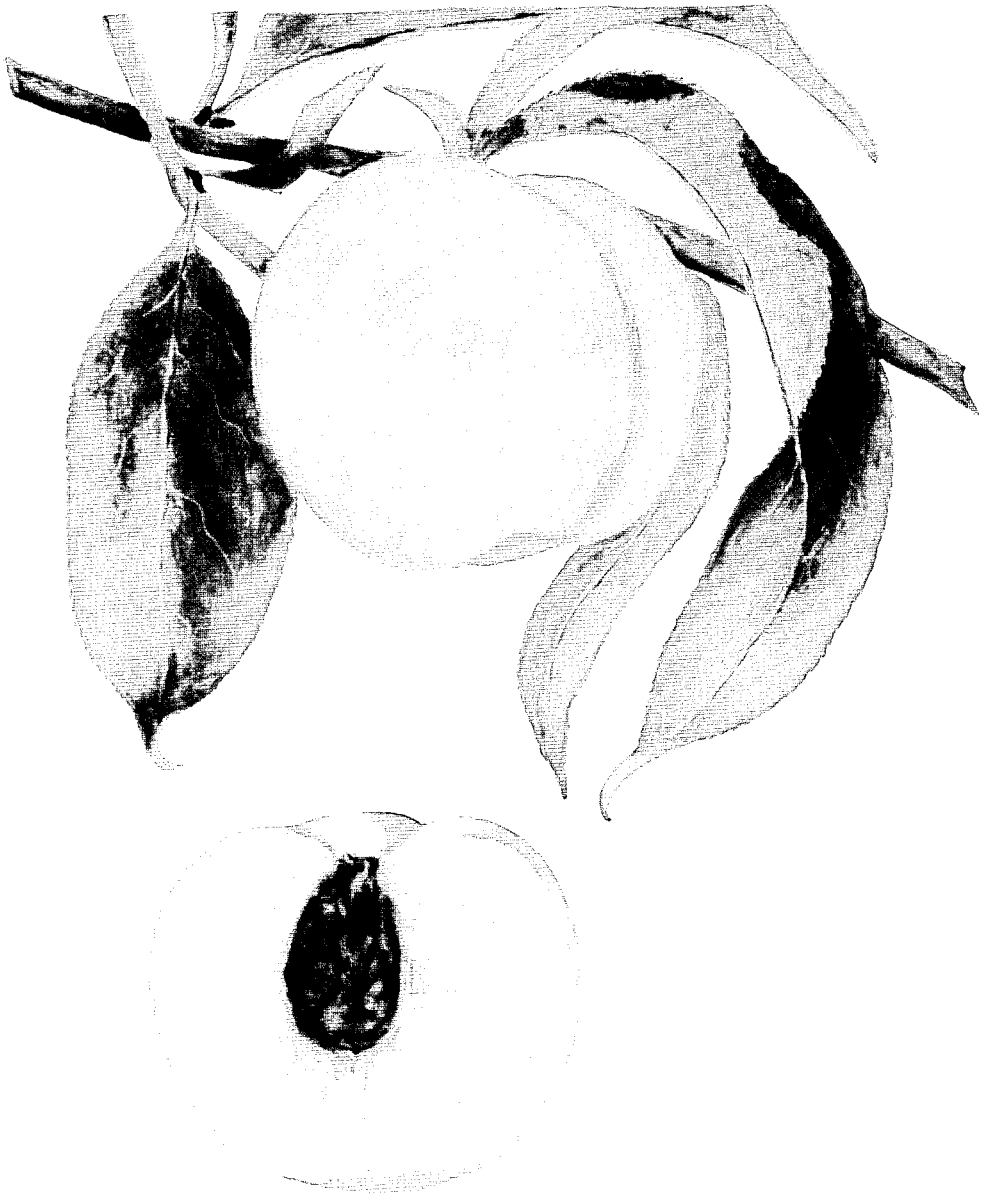
GRANT MERRILL
INVENTOR
Vergil L. Gerard
ATTORNEY United States Patent Office Plant Pat. 2,965
Patented Jan. 27, 1970

2,965
PEACH TREE

Grant Merrill, Tulare County, Calif.
(416 N. Anderson Road, Exeter, Calif. 93221)

Filed May 20, 1968, Ser. No. 730,686
Int. Cl. A01h 5/08
U.S. Cl. Plt.—43 1 Claim The present invention relates to a peach tree and more particularly to a new and distinct variety thereof broadly characterized by its large tree producing heavy yields of large fruit with highly colored skin and firm flesh to make it well adapted for shipping long distances and with flesh that is completely free from the stone, and with buttery textured flesh and with clear yellow color throughout except for a clear separation of red color near the stone, and therefore showing excellent quality for freezing purposes.

The instant variety is most nearly like Parade (U.S. Plant Patent No. 2,153) but is an improvement thereon in that the tree produces heavier yields of larger sized fruit that is better adapted for freezing because of its cleared yellow flesh and its confinement of the red to the area around the stone and its buttery textured flesh.

I originated the present variety on a farm at Red Bluff, Calif. (Tehama County), formerly owned by me by crossing the J. H. Hale (unpatented) variety of peach with an open pollinated, third generation selection of a cross of J. H. Hale with Levi Cling (unpatented). It can be expressed as J. H. Hale × (J. H. Hale × Levi Cling F3).

The accompanying drawing is an oil painting of a characteristic twig of the subject peach tree bearing foliage and a mature fruit, and additionally, showing a fruit of the subject variety divided on its suture plane to reveal flesh coloration and stone characteristics.

Referring more specifically to the pomological characteristics of this new and distinct variety of peach tree, the following has been observed under the ecological conditions prevailing at Exeter, Tulare County, Calif. and is an outline description thereof. All major color plate identifications are by reference to Maerz and Paul, Dictionary of Color, first edition.

TREE

Shape: Large, medium spreading, very productive, regular bearer.

Trunk: Medium in dimensions, gray color.

Branches: Medium in dimensions, gray on the older limbs, brown on the younger limbs, lenticels numerous and medium to large in size.

Leaves: Generally large, 4½ to 7½ inches long, 1¼ to 2 inches in width, lanceolate tip acuminate, medium thick, moderately crinkled, color dark to medium green 32–L–12 to 31–A–11 on the upper surface, light green 19–J–5 on the under surface; margins, crenate; petiole medium length, medium slender, deciduous.

Glands: Reniform, opposite, large, two to seven in number, at base of leaf and on petiole.

FLOWER BUDS

Medium size, plump, round, free, pubescent.

FLOWERS

Medium to late in season, in 1968, an early blooming season, first blooms February 28, full bloom March 7; small in size pink, pollen abundant.

FRUIT

General: Firm ripe when described Sept. 24, 1967, a very late season.

Size: Large, variable 2½ to 3½ inches axially, 2¾ to 3½ inches in suture plane, 2½ to 3½ inches at right angles to suture plane, generally globose.

Suture: Distinct, shallow, extends from base to slightly beyond apex.

Ventral surface: Rounded, slightly throughout on both sides.

Dorsal side: Rounded.

Cavity: Flaring, elongated in suture plane with suture showing on both sides on most, depth 7/16 to 11/16, breadth ¾ to 1⅜ inches, yellow with red markings on many.

Base: Obcordate.

Apex: Retuse, pistil point generally very small, depressed.

Stem: Length average ¼ inch, diameter average ⅛ inch, adheres to stone in some fruit.

Skin: Medium thick, medium tender, tenacious to flesh pubescence scant, short.

Color: Medium yellow undertone 10–L–5 to darker yellow overtone 10–L–10 overlaid on about half the surface on fruit exposed to the sun with light red 5–K–6 to dark red 7–H–6.

Flesh: Color light yellow undertone 10–K–1 to darker overtones 10–L–7 and showing a bright red 6–L–6 near the stone, Amygdalin, moderate; juice, moderate; texture, meaty and buttering; fiber, few, fine, tender; ripens, evenly; flavor, distinct and pleasant; aroma, mild; eating quality, good.

Stone: Adheres to flesh. Completely free when firm ripe or soft ripe.

Fibers: Few, short.

Size: Medium size, length 1 1/16 to 1¾ inches, breadth generally about one inch, thickness ⅝ to 1 inch.

Form: Obovate, tip acuminate.

Base: Oval.

Apex: Acuminate with a notch ½ to ¾ inch long on the dorsal side of the apex on most stones.

Sides: Unequal, generally flattened on either side.

Surface: Irregularly furrowed and pitted.

Pits: Usually elongated, some round.

Ventral ridge: Thick, with many small furrows and ridges.

Dorsal edge: Usually one deep furrow with ridges on both sides, usually discontinuous at apex.

Tendency to split: Slight.

Color: Shades of brown, 15–L–12 to 48–L–12.

Use: Market, nearby and distant, fresh markets, and commercial freezing.

Keeping quality: Good.

Shipping quality: Good.

Although the new variety of peach tree possesses the described characteristics under the growing condition in Exeter, Tulare County, Calif., having been first observed near Red Bluff, Tehama County, Calif., it is to be understood that variation of the usual magnitude in the characteristics incident to the growing conditions, fertilization, pruning, and pest control is to be expected.

Having thus described and illustrated my new variety of peach tree, what is claimed is:

1. A new and distinct variety of peach tree substantially as illustrated and described and which is characterized by a large tree producing heavy yields of large fruit with highly colored skin and firm flesh to make it a good shipping peach for long distance shipment, and with flesh that is completely free from the stone and has buttery texture with clear yellow color throughout except for a clear separation of bright red color near the stone, thus possessing excellent quality for freezing purposes, and most nearly resembling the Parade (U.S. Plant Patent No. 2,153) but distinguished therefrom in producing heavier yields of larger size fruit which is better adapted for freezing because of its clear yellow colored and buttery textured flesh and its confinement of the red colored area around the stone to close proximity with the stone.

No references cited.

ROBERT E. BAGWILL, Primary Examiner